US006872540B2

(12) United States Patent
Boone et al.

(10) Patent No.: US 6,872,540 B2
(45) Date of Patent: Mar. 29, 2005

(54) **METHOD AND APPARATUS FOR DISTINGUISHING CROHN'S DISEASE FROM ULCERATIVE COLITIS AND OTHER GASTROINTESTINAL DISEASES BY DETECTING THE PRESENCE OF FECAL ANTIBODIES TO *SACCHAROMYCES CEREVISIAE***

(75) Inventors: James Hunter Boone, Christiansburg, VA (US); David Maxwell Lyerly, Radford, VA (US); Tracy Dale Wilkins, Riner, VA (US)

(73) Assignee: Techlab, Inc., Blacksburg, VA (US)

( * ) Notice: Subject to any disclaimer, the term of this patent is extended or adjusted under 35 U.S.C. 154(b) by 0 days.

(21) Appl. No.: 10/280,564

(22) Filed: Oct. 25, 2002

(65) Prior Publication Data

US 2003/0143649 A1 Jul. 31, 2003

Related U.S. Application Data

(60) Provisional application No. 60/335,812, filed on Oct. 26, 2001.

(51) Int. Cl.$^7$ .............................................. G01N 33/53
(52) U.S. Cl. ........................ 435/7.1; 435/7.2; 435/7.31; 435/7.72; 435/7.92; 435/975
(58) Field of Search ................................ 435/7.1, 7.31, 435/7.72, 7.92, 975, 7.2

(56) References Cited

U.S. PATENT DOCUMENTS

| 5,359,038 A | 10/1994 | Padron .................... 530/390.5 |
| 5,932,429 A | 8/1999 | Targan et al. .............. 435/7.24 |
| 5,968,741 A | 10/1999 | Plevy et al. .................. 435/6 |
| 6,218,129 B1 | 4/2001 | Walsh et al. ............... 435/7.21 |

FOREIGN PATENT DOCUMENTS

| WO | WO 97/39356 | 10/1997 |
| WO | WO 98/46997 | 10/1998 |
| WO | WO 99/60403 | 11/1999 |
| WO | WO 01/11334 A2 | 2/2001 |

OTHER PUBLICATIONS

HCAPLUS Abstrcat of US 6667160 (one page).*
R. Barnes, S. Allan, C. Taylor–Robinson, R. Finn, P. Johnson, "Serum Antibodies Reactive with *Saccharomyces cerevisiae* in Inflammatory Bowel Disease: Is IgA Antibody a Marker for Crohn's Disease?" *Int Arch Allergy Appl Immunol* (1990) 92, 9–15.
C. Faille, D. Mackenzie, J. Michalski, and D. Poulain, "Evaluation of an Enzyme Immunoassay Using Neoglycolipids Constructed from *Candida albicans* Oligomannosides to Define the Specificity of Anti–Mannan Antibodies" *Eur. J. Clin. Microbiol. Infect. Dis.*, (1992) May, 438–446.
M. Giaffer and C. Holdsworth, "Antibodies to *Saccharomyces cerevisiae* in patients with Crohn's disease and their possible pathogenic importance" *Gut* (1992) 33, 1071–1075.

S. Hanaues, "Inflammatory Bowel Disease" *The New England Journal of Medicine* (1996) 334, 841–848.
Hauther and G. D'Haens, "Medical Management of Ulcerative Colitis" in Targan and Shanahan Inflammatory Bowel Disease: From Bench to Bedside, *Williams and Wilkens* (1994) 545–561.
C. Jongeneel, L. Briant, I. Udalova, A. Sevin, S. Nedospasov, and A. Thomsen, "Extensive genetic polymorphism in the human tumor necrosis factor region and relation to extended HLA haplotypes" *Proc. Natl. Acad. Sci. USA* (1991) 88, 9717–9721.
E. Lindberg, K. Magnusson, C. Tysk, and G. Jarnerot, "Antibody (IgG, IgA, and IgM) to baker's yeast *Saccharomyces cerevisiae*), yeast mannan, gliadin, ovalbumin and betalactoglobulin in monozygotic twins with inflammatory bowel disease" *Gut* (1991) 909–913.
J. Main, H. McKenzie, G. Yeaman, M. Kerr, D. Robson, C. Pennington, and D. Parratt, "Antibody to *Saccharomyces cerevisiae* (bakers' yeast) in Crohn's disease" *BMJ* (1988) 297 1105–1106.
H. McKenzie, J. Main, C. Pennington, and D. Parratt, "Antibody to selected strains of *Saccharomyces cerevisiae* (baker's and brewer's yeast) and *Candida albicans* in Crohn's disease" *Gut* (1990) 31, 537–538.
H. McKenzie, D. Parratt, J. Main, and C. Pennington, "Antigenic heterogeneity of strains of *Saccharomyces cerevisiae* and *Candida albicans* recognized by serum antibodies from patients with Crohn's disease" *FEMS Microbiology Immunology* (1992) 89, 219–224.
H. Yang, J. Rotter, H. Toyoda, C. Landers, D. Tyan, C. McElree, and S. Targan, "Ulcerative Colitis: A Genetically Heterogeneous Disorder Defined by Genetic (HLA Class II) and Subclinical (Antineutrophil Cytoplasmic Antibodies) Markers" *The American Society for Clinical Investigation, Inc.* (1993) 92, 1080–1084.
C. Young, A. Sonnenberg, and E. Burns, "Lymphocyte Proliferation Response to Baker's Yeast in Crohn's Disease" *Digestion* (1994) 55, 40–43.

(Continued)

*Primary Examiner*—S. Devi
(74) *Attorney, Agent, or Firm*—Shook, Hardy & Bacon, L.L.P.

(57) ABSTRACT

A method and apparatus for the differentiation of Crohn's disease from other gastrointestinal illnesses, such as ulcerative colitis and irritable bowel syndrome, using the presence of fecal anti-*Saccharomyces cerevisiae* antibodies (ASCA) as a marker for Crohn's disease are provided. The apparatus includes an enzyme-linked immunoassay or other immunoassay that utilizes antibodies specific to human immunoglobins for the measurement of total endogenous ASCA in a human fecal sample. The method and apparatus may be used by healthcare providers to distinguish Crohn's disease from other gastrointestinal illnesses, such as ulcerative colitis and irritable bowel syndrome.

15 Claims, 1 Drawing Sheet

OTHER PUBLICATIONS

M. Giaffer, A. Clark, C. Holdsworth, "Antibodies against *Saccharomyces Cervisiae* (Baker's & Brewer's yeast) in Crohn's Disease" *Gastorenterology* (1991) 100, No. 5, Part 2.

G. Barclay, H. McKenzie, J. Pennington, D. Parratt, and C. Pennington, "The Effect of Dietary Yeast on the Activity of Stable Chronic Crohn's Disease" *Scand J Gastroenterol* (1992) 27, 196–200.

M. Broker, H. Harthus, and R. Barnes, "A murine monoclonal antibody directed against a yeast cell wall glycoprotein antigen of the yeast genus *Saccharomyces*" FEMS Microbiology Letters (1994) 118, 297–304.

C. Darroch, S. Christmas, and R. Barnes, "*In vitro* human lymphocyte proliferative responses to a glycoprotein of the yeast *Saccharomyces cerevisiae*" *Immunology Letters* (1994) 81, 247–252.

B. Heelan, S. Allan, and R. Barnes, "Identification of a 200-kDa glycoprotein antigen of *Saccharomyces cerevisiae*" *Immunology Letters* (1991) 28, 181–186.

C. Galperin and M. Gershwin, Immunopathogenesis of Gastrointestinal and Hepatobiliary Diseases, *JAMA*, (1997) 278, 1946–1955.

R. Barnes, S. Allan, C. Robinson, R. Finn, and P. Johnson, "Serum Antibodies Reactive with *Saccharomyces cerevisiae* in Inflammatory Bowel Disease: Is IgA Antibody a Merker for Crohn's Disease?" *Int. Arch. Allergy Appl. Immuno* (1990) 92, 9–15.

J. Colomber, B. Sendid, J. Quinton, P. Jacquinot, O. Goulet, A Cortot, D. Poulain, "Anti–*Saccharomyces cerevisiae* Antibodies: A New Subclinical Marker for Crohn's Disease" *Gastroenterology* (1996) 110, No. 4.

N. Oshitani, et al., IgG subclasses of anti *Saccharomyces cerevisiae* antibody in inflammatory bowel disease; Blackwell Science Ltd., European Journal of Clinical Investigation, vol. 31, pp. 221–225, 2001.

* cited by examiner

METHOD AND APPARATUS FOR DISTINGUISHING CROHN'S DISEASE FROM ULCERATIVE COLITIS AND OTHER GASTROINTESTINAL DISEASES BY DETECTING THE PRESENCE OF FECAL ANTIBODIES TO *SACCHAROMYCES CEREVISIAE*

CROSS-REFERENCE TO RELATED APPLICATIONS

This application claims the benefit of priority to U.S. Provisional Application No. 60/335,812 filed on Oct. 26, 2001, the entirety of the disclosure of which is hereby incorporated by reference.

STATEMENT REGARDING FEDERALLY SPONSORED RESEARCH OR DEVELOPMENT

Not Applicable.

FIELD OF THE INVENTION

A method and apparatus for the differentiation of Crohn's disease from other gastrointestinal illnesses, such as ulcerative colitis and irritable bowel syndrome, using the presence of fecal anti-*Saccharomyces cerevisiae* antibodies (ASCA) as a marker for Crohn's disease are provided. The apparatus includes an enzyme-linked immunoassay or other immunoassay that utilizes antibodies specific to human immunoglobulins for the measurement of total endogenous ASCA in a human fecal sample. The method and apparatus may be used by healthcare providers to distinguish Crohn's disease from other gastrointestinal illnesses, such as ulcerative colitis and irritable bowel syndrome.

BACKGROUND OF THE INVENTION

It is estimated that at least one million Americans suffer from Inflammatory Bowel Disease (IBD). IBD is characterized by a chronic inflammatory response that results in histologic damage to the intestinal lining. IBD comprises two known clinical subtypes, Crohn's Disease (CD) and ulcerative colitis (UC). CD may involve the entire gastrointestinal tract and include inflammation extending into the transmural mucosa whereas UC affects solely the large bowel and includes inflammation of the innermost lining. Due to the differences between them, these two distinct diseases require a rapid differential diagnosis for optimal treatment. Conventional methods for differentiating between these clinical subtypes of IBD utilize multiple endoscopy examinations and histological analysis. These methods, however, do not permit quick differential diagnosis as each may require years for a diagnosis to be confirmed. As a result, methods are needed for the rapid differential diagnosis of CD and UC.

Serological methods for the differential diagnosis of CD and UC are known in the art. For example, it is known in the art to use the presence of serum anti-*Saccharomyces cerevisiae* antibodies (ASCA) to diagnose CD. See Main et al., Antibody to *Saccharomyces cerevisiae* (baker's yeast) in Crohn's disease, BMJ Vol. 297 (Oct. 29, 1988); Broker et al., A Murine Monoclonal Antibody Directed Against a Yeast Cell Wall Glycoprotein Antigen of the Yeast Genus Saccharomyces, FEMS Microbiology Letters 118 (1994), 297-304. It is further known in the art to use the presence of serum ASCA to diagnose clinical subtypes of UC and CD in patients presenting with established diagnoses. For example, U.S. Pat. No. 5,968,741 discloses utilizing the presence of serum ASCA to diagnose a medically resistant clinical subtype of UC in patients presenting with an established diagnosis of UC. Similarly, U.S. Pat. No. 5,932,429 discloses utilizing the presence of serum ASCA to diagnose a clinical subtype of CD in patients presenting with an established diagnosis of CD.

Each of the above-mentioned serological methods utilizing ASCA as a marker has a number of drawbacks. For instance, each method requires an invasive procedure such as a finger prick or the like to obtain a serum sample. Further, each method utilizes only serum antibodies that are not required to cross the intestinal wall and the serum antibodies may not be accurate indicator for the proper diagnosis.

SUMMARY OF THE INVENTION

A method for testing a fecal sample, the method comprising: obtaining a fecal sample from a person; and determining the amount of anti-*Saccharomyces cerevisiae* antibodies in the sample.

A method for testing a fecal sample, the method comprising: obtaining a fecal sample from a person; and determining the presence of anti-*Saccharomyces cerevisiae* antibodies in the sample, wherein the presence of fecal anti-*Saccharomyces cerevisiae* antibodies is used to aid in the differentiation of Crohn's disease from other gastrointestinal illnesses such as, ulcerative colitis and irritable bowel syndrome (IBS).

An assay for determining the concentration of endogenous anti-*Saccharomyces cerevisiae* antibodies, the assay comprising: obtaining a human fecal sample; diluting the fecal sample; contacting the sample with extract of *Saccharomyces cerevisiae* to create a treated sample; contacting the treated sample with enzyme-linked polyclonal antibodies to create a readable sample; determining the optical density of the readable sample at 450 nm; generating a purified anti-*Saccharomyces cerevisiae* antibodies standard curve; and comparing the optical density of the readable sample to the standard curve to determine the concentration of endogenous anti-*Saccharomyces cerevisiae* antibodies in the fecal sample.

A diagnostic assay for diagnosing Crohn's disease by determining the level of endogenous anti-*Saccharomyces cerevisiae* antibodies, the assay comprising: obtaining a human fecal sample; diluting the sample; contacting the sample extract *Saccharomyces cerevisiae* to create a treated sample; contacting the treated sample with enzyme-linked polyclonal antibodies to create a readable sample; adding an enzyme substrate for color development and determining the optical density of the readable sample at 450 nm to determine whether the readable sample contains an elevated level of endogenous anti-*Saccharomyces cerevisiae* antibodies as compared to a reference value for healthy control subjects.

A kit for diagnosing Crohn's disease by testing a fecal sample from a person to be diagnosed, the kit comprising: one or more microassay plates, each the plate containing extract *Saccharomyces cerevisiae*; enzyme-linked polyclonal antibody to human anti-*Saccharomyces cerevisiae* antibodies; and enzyme substrate for color development.

Additional aspects of invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

DETAILED DESCRIPTION OF THE INVENTION

Figure 1:
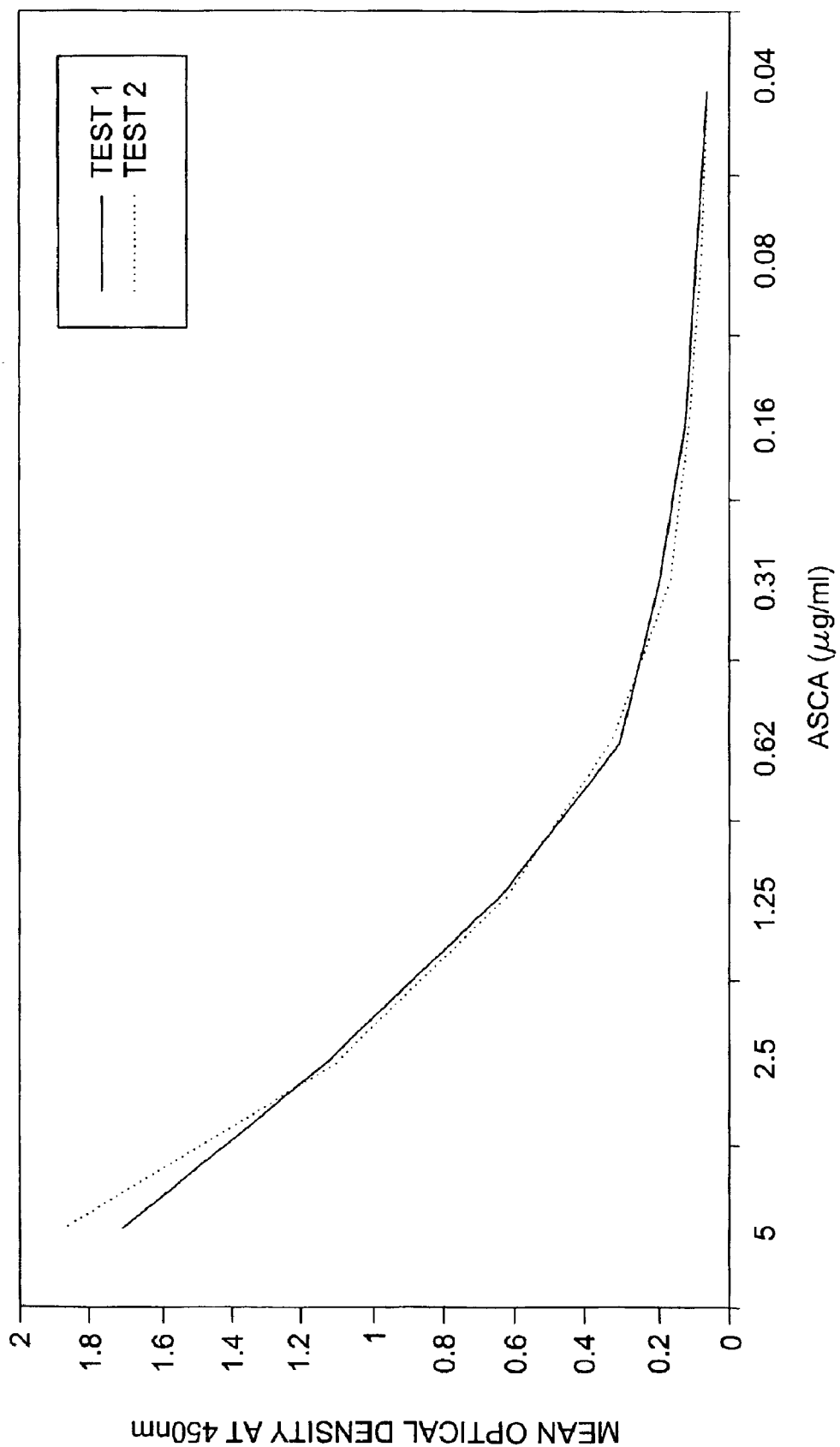
FIG. 1 is a graphical representation of a standard curve of purified anti-*Saccharomyces cerevisiae* antibodies.

A method and apparatus for the differentiation of Crohn's disease from other gastrointestinal illnesses, such as ulcerative colitis and irritable bowel syndrome, using the presence of fecal anti-*Saccharomyces cerevisiae* antibodies (ASCA) as a marker for Crohn's disease are provided. The apparatus includes an enzyme-linked immunoassay or other immunoassay that utilizes antibodies specific to human immunoglobulins for the measurement of total endogenous ASCA in a human fecal sample. The method and apparatus may be used by healthcare providers to distinguish Crohn's disease from other gastrointestinal illnesses, such as ulcerative colitis and irritable bowel syndrome. The particular embodiments described herein are intended in all respects to be illustrative rather than restrictive. Alternative embodiments will become apparent to those skilled in the art to which the present embodiment of the invention pertains without departing from its scope.

The present embodiment of the invention provides immunoassays, including, but not limited to, enzyme-linked immunoassays (ELISAs), that utilize antibodies specific to human ASCA for the measurement of total endogenous ASCA in fecal samples, including feces and mucosal secretions. The assay of the present invention may include, but is not limited to, the following steps: 1) obtaining a fecal sample from a person to be diagnosed, 2) diluting the sample, 3) contacting the sample with extract of *Saccharomyces cerevisiae* to create a treated sample, and 4) contacting the treated sample with enzyme-linked polyclonal antibodies to create a readable sample. Further, the optical density of the readable sample at 450 nm may be determined. The optical density of the readable sample then may be compared to a standard curve generated using purified anti-*Saccharomyces cerevisiae* standard curve to determine the concentration of the endogenous anti-*Saccharomyces cerevisiae* antibodies in the fecal sample. The present embodiment of the invention further provides a kit usable in such immunoassays to aid physicians and other clinical personnel in diagnosing Crohn's disease.

It will be understood and appreciated by those of skill in the art that a immunoassay such as a lateral flow dipstick that utilizes both monoclonal and polyclonal antibodies to total endogenous ASCA also may be used to diagnose Crohn's disease. Such is contemplated to be within the scope hereof.

A limited number of cases of ulcerative colitis and IBS may test positive for ASCA. Therefore, it is possible that a diagnosis of Crohn's disease cannot be established solely on the basis of a positive result with the assay of the present embodiment of the invention. However, a positive result with the assay of the present embodiment of the invention will permit the substantial preclusion of a diagnosis of a other gastrointestinal illness, such as IBS or ulcerative colitis.

The immunoassay of the embodiment of the present embodiment of the invention may be used as an in vitro diagnostic aid for detecting elevated levels of ASCA as a detection marker for Crohn's disease. The immunoassay of the present embodiment of the invention provides a test that is easy to use, simple to read, and accurate for distinguishing Crohn's disease from IBS or ulcerative colitis.

The following examples are intended in all respects to be illustrative rather than restrictive.

EXAMPLE 1

In this example using an ELISA method, a fecal sample was obtained and serially diluted 20 fold. 100 µl of the diluted sample was added to a test well of a microassay plate coated with extract of *Saccharomyces cerevisiae* and purified mannan. The sample then was incubated at 37° C. to allow antibodies to *Saccharomyces cerevisiae* to bind to the extract of *Saccharomyces cerevisiae*. Following incubation, anti-human Ig polyclonal antibodies coupled to horseradish peroxidase enzyme (conjugate) were added to the test well and allowed to bind to captured ASCA. Unbound conjugate then was washed from the well and one component substrate (tetra-methyl-benzidene and hydrogen peroxide) was added for color development. Following the substrate incubation, 0.1M sulfuric acid was added to quench the reaction and the optical density (OD) was obtained spectrophotometrically at 450 nm using a single wavelength spectrophotometer.

The method described above was used in a clinical study to test a total of 86 IBD patients (55.8% males and 44.2% females). The approximate 1 to 1 ratio of males to females was similar to the ratio observed in IBD patient populations. The IBS patient group ranged in age from 19 to 78 years and was 9% male and 91% female. This ratio of males to females (1:10) reflects the increased incidence for IBS in females as seen in patient populations. The healthy control (HC) patient group ranged in age from 20 to 79 years old and was 33.3% male and 66.6% female. A summary of the patient population in the clinical study is shown in Table 1.

TABLE 1

Summary of patient population.

| Summary of Clinical Histories (N = 120) | Total Subjects |
|---|---|
| Total number of IBD patients | 86 |
| No. Males | 48 |
| No. Females | 38 |
| Total number of patients with Crohn's Disease | 49 |
| No. Males | 26 |
| No. Females | 23 |
| Total number of patients with ulcerative colitis | 37 |
| No. Males | 22 |
| No. Females | 15 |
| Total number of patients with irritable bowel syndrome | 22 |
| No. Males | 2 |
| No. Females | 20 |
| Total number of healthy controls | 12 |
| No. Males | 4 |
| No. Females | 8 |

In the clinical study, there were 37 ulcerative colitis patients, 49 Crohn's disease patients, 22 irritable bowel patients, and 12 healthy controls. Fecal samples were collected from each enrolled subject and stored at −70° C. until tested. The optical densities for each sample were determined using the method described above. Results were reported as positive for fecal ASCA if an optical density of greater than or equal to 0.200 was observed. Results were reported as negative for fecal ASCA if an optical density of less than or equal to 0.199 was observed. Other clinical data, such as stool consistency, was also determined. Table 2, below, contains the clinical data and test results for healthy patients that participated in this clinical study. Table 3, below, contains the clinical data and test results for patients with ulcerative colitis patients that participated in this clinical study. Table 4, below, contains the clinical data and test results for patients with Crohn's disease that participated in this study. Table 5, below, contains the clinical data and test results for patients with irritable bowel syndrome that participated in this study.

TABLE 2

Clinical data and test results for healthy controls

| Donor ID | Sex | Age Range | Previous of chronic GI illness | Stool Consistency | Optical Density | Fecal ASCA |
|---|---|---|---|---|---|---|
| HC1 | F | 40–49 | NO | Solid | 0.098 | NEGATIVE |
| HC2 | F | 40–49 | NO | Solid | 0.089 | NEGATIVE |
| HC3 | M | 70–79 | NO | Solid | 0.095 | NEGATIVE |
| HC4 | F | 60–69 | NO | Solid | 0.085 | NEGATIVE |
| HC5 | M | 70–79 | NO | Solid | 0.083 | NEGATIVE |
| HC6 | F | 70–79 | NO | Solid | 0.076 | NEGATIVE |
| HC7 | F | 50–59 | NO | Solid | 0.124 | NEGATIVE |
| HC8 | F | 40–49 | NO | Solid | 0.095 | NEGATIVE |
| HC9 | F | 50–49 | NO | Solid | 0.111 | NEGATIVE |
| HC10 | F | 40–49 | NO | Solid | 0.111 | NEGATIVE |
| HC11 | M | 50–60 | NO | Solid | 0.070 | NEGATIVE |
| HC12 | M | 50–60 | NO | Solid | 0.054 | NEGATIVE |

TABLE 3

Clinical data and test results for ulcerative colitis patients

| Patient ID | Sex | Age | Disease | Stool Consistency | Disease Activity | Optical Density | Fecal ASCA |
|---|---|---|---|---|---|---|---|
| UC1 | F | 46 | UC | Liquid | ACTIVE | 0.184 | NEGATIVE |
| UC2 | M | 39 | UC | Liquid | ACTIVE | 0.378 | POSITIVE |
| UC3 | F | 30 | UC | Semi-Solid | ACTIVE | 0.193 | NEGATIVE |
| UC4 | F | 31 | UC | Semi-Solid | INACTIVE | 0.319 | POSITIVE |
| UC5 | F | 30 | UC | Semi-Solid | ACTIVE | 0.114 | NEGATIVE |
| UC6 | M | 61 | UC | Semi-Solid | INACTIVE | 0.115 | NEGATIVE |
| UC7 | F | 68 | UC | Liquid | INACTIVE | 0.091 | NEGATIVE |
| UC8 | F | 45 | UC | Liquid | ACTIVE | 0.356 | POSITIVE |
| UC9 | F | 21 | UC | Semi-Solid | ACTIVE | 0.082 | NEGATIVE |
| UC10 | F | 27 | UC | Liquid | ACTIVE | 0.161 | NEGATIVE |
| UC11 | F | 24 | UC | Solid | INACTIVE | 0.104 | NEGATIVE |
| UC12 | F | 74 | UC | Semi-Solid | INACTIVE | 0.091 | NEGATIVE |
| UC13 | M | 69 | UC | Semi-Solid | ACTIVE | 0.070 | NEGATIVE |
| UC14 | M | 19 | UC | Solid | INACTIVE | 0.088 | NEGATIVE |
| UC15 | M | 62 | UC | Solid | INACTIVE | 0.054 | NEGATIVE |
| UC16 | F | 70 | UC | Solid | INACTIVE | 0.056 | NEGATIVE |
| UC17 | M | 23 | UC | Liquid | ACTIVE | 0.573 | POSITIVE |
| UC18 | F | 52 | UC | Solid | ACTIVE | 0.073 | NEGATIVE |
| UC19 | M | 60 | UC | Solid | INACTIVE | 0.062 | NEGATIVE |
| UC20 | F | 52 | UC | Liquid | ACTIVE | 0.089 | NEGATIVE |
| UC21 | M | 31 | UC | Solid | INACTIVE | 0.064 | NEGATIVE |
| UC22 | M | 44 | UC | Semi-Solid | INACTIVE | 0.143 | NEGATIVE |
| UC23 | F | 30 | UC | Liquid | ACTIVE | 0.110 | NEGATIVE |
| UC24 | M | 48 | UC | Semi-Solid | INACTIVE | 0.096 | NEGATIVE |
| UC25 | F | 37 | UC | Liquid | ACTIVE | 0.282 | POSITIVE |
| UC26 | F | 32 | UC | Solid | ACTIVE | 0.107 | NEGATIVE |
| UC27 | F | 46 | UC | Liquid | ACTIVE | 0.199 | NEGATIVE |
| UC28 | M | 49 | UC | Semi-Solid | INACTIVE | 0.161 | NEGATIVE |
| UC29 | F | 42 | UC | Solid | INACTIVE | 0.080 | NEGATIVE |
| UC30 | F | 41 | UC | Semi-Solid | INACTIVE | 0.087 | NEGATIVE |
| UC31 | F | 43 | UC | Solid | INACTIVE | 0.070 | NEGATIVE |
| UC32 | M | 30 | UC | Solid | ACTIVE | 0.103 | NEGATIVE |
| UC33 | F | 43 | UC | Solid | INACTIVE | 0.092 | NEGATIVE |
| UC34 | F | 33 | UC | Semi-Solid | INACTIVE | 0.075 | NEGATIVE |
| UC35 | M | 58 | UC | Semi-Solid | ACTIVE | 0.121 | NEGATIVE |
| UC36 | F | 32 | UC | Semi-Solid | ACTIVE | 0.083 | NEGATIVE |

TABLE 4

Clinical Data and test results for Crohn's disease patients.

| Patient ID | Sex | Age | Disease | Stool Consistency | Disease Activity | Optical Density | FECAL ASCA |
|---|---|---|---|---|---|---|---|
| CD1 | M | 26 | CD | Liquid | INACTIVE | 1.900 | POSITIVE |
| CD2 | M | 60 | CD | Liquid | ACTIVE | 2.849 | POSITIVE |
| CD3 | F | 66 | CD | Liquid | ACTIVE | 0.282 | POSITIVE |
| CD4 | F | 74 | CD | Semi-Solid | INACTIVE | 0.091 | NEGATIVE |

TABLE 4-continued

Clinical Data and test results for Crohn's disease patients.

| Patient ID | Sex | Age | Disease | Stool Consistency | Disease Activity | Optical Density | FECAL ASCA |
|---|---|---|---|---|---|---|---|
| CD5 | F | 25 | CD | Solid | INACTIVE | 0.162 | NEGATIVE |
| CD6 | F | 66 | CD | Semi-Solid | INACTIVE | 1.240 | POSITIVE |
| CD7 | M | 39 | CD | No Data | ACTIVE | 1.150 | POSITIVE |
| CD8 | F | 46 | CD | Liquid | ACTIVE | 0.160 | NEGATIVE |
| CD9 | F | 46 | CD | Semi-Solid | INACTIVE | 0.074 | NEGATIVE |
| CD10 | F | 56 | CD | Solid | ACTIVE | 0.406 | POSITIVE |
| CD11 | M | 56 | CD | Solid | ACTIVE | 0.168 | NEGATIVE |
| CD12 | F | 56 | CD | Liquid | ACTIVE | 0.732 | POSITIVE |
| CD13 | M | 21 | CD | Solid | ACTIVE | 1.369 | POSITIVE |
| CD14 | M | 52 | CD | Semi-Solid | INACTIVE | 0.136 | NEGATIVE |
| CD15 | M | 63 | CD | Solid | INACTIVE | 0.134 | NEGATIVE |
| CD16 | M | 34 | CD | Solid | ACTIVE | 0.076 | NEGATIVE |
| CD17 | F | 45 | CD | Semi-Solid | ACTIVE | 0.160 | NEGATIVE |
| CD18 | M | 67 | CD | Semi-Solid | INACTIVE | 0.059 | NEGATIVE |
| CD19 | F | 46 | CD | No Data | ACTIVE | 0.839 | POSITIVE |
| CD20 | M | 66 | CD | Semi-Solid | INACTIVE | 0.084 | NEGATIVE |
| CD21 | M | 63 | CD | Liquid | ACTIVE | 0.780 | POSITIVE |
| CD21 | M | 51 | CD | Semi-Solid | ACTIVE | 3.000 | POSITIVE |
| CD22 | M | 34 | CD | Semi-Solid | ACTIVE | 1.447 | POSITIVE |
| CD23 | M | 21 | CD | Solid | ACTIVE | 2.757 | POSITIVE |
| CD24 | F | 78 | CD | Semi-Solid | INACTIVE | 0.092 | NEGATIVE |
| CD25 | F | 27 | CD | Semi-Solid | ACTIVE | 0.979 | POSITIVE |
| CD26 | M | 40 | CD | Liquid | ACTIVE | 0.373 | POSITIVE |
| CD27 | M | 51 | CD | Liquid | ACTIVE | 0.978 | POSITIVE |
| CD28 | M | 42 | CD | Liquid | ACTIVE | 0.089 | NEGATIVE |
| CD29 | F | 31 | CD | Solid | INACTIVE | 0.075 | NEGATIVE |
| CD30 | F | 59 | CD | Solid | ACTIVE | 0.088 | NEGATIVE |
| CD31 | M | 35 | CD | Semi-Solid | ACTIVE | 1.487 | POSITIVE |
| CD32 | M | 37 | CD | Semi-Solid | INACTIVE | 1.257 | POSITIVE |
| CD33 | F | 77 | CD | Solid | INACTIVE | 0.093 | NEGATIVE |
| CD34 | F | 40 | CD | No Data | ACTIVE | 1.762 | POSITIVE |
| CD35 | F | 38 | CD | Liquid | ACTIVE | 0.098 | NEGATIVE |
| CD36 | M | 51 | CD | Liquid | ACTIVE | 2.326 | POSITIVE |
| CD37 | M | 38 | CD | Semi-Solid | ACTIVE | 0.091 | NEGATIVE |
| CD38 | M | 37 | CD | Liquid | ACTIVE | 0.372 | POSITIVE |
| CD39 | M | 59 | CD | Semi-Solid | ACTIVE | 0.224 | POSITIVE |
| CD40 | F | 41 | CD | Solid | ACTIVE | 0.503 | POSITIVE |
| CD41 | M | 41 | CD | Solid | ACTIVE | 0.117 | NEGATIVE |
| CD42 | M | 48 | CD | Liquid | ACTIVE | 0.115 | NEGATIVE |
| CD43 | F | 40 | CD | Solid | INACTIVE | 0.638 | POSITIVE |
| CD44 | F | 72 | CD | Solid | ACTIVE | 0.087 | NEGATIVE |
| CD45 | F | 32 | CD | Liquid | INACTIVE | 0.911 | POSITIVE |
| CD46 | F | 24 | CD | Liquid | ACTIVE | 0.341 | POSITIVE |
| CD47 | M | 23 | CD | Solid | INACTIVE | 0.088 | NEGATIVE |
| CD48 | F | 34 | CD | Liquid | ACTIVE | 0.599 | POSITIVE |

TABLE 5

Clinical data and test results for irritable bowel syndrome patients

| Patient ID | Sex | Age | Disease | Stool consistency | Disease Activity | Optical Density | Fecal ASCA |
|---|---|---|---|---|---|---|---|
| IBS1 | F | 56 | IBS | Semi-Solid | ACTIVE | 0.132 | NEGATIVE |
| IBS2 | F | 48 | IBS | Solid | ACTIVE | 0.103 | NEGATIVE |
| IBS3 | F | 30 | IBS | Solid | ACTIVE | 0.073 | NEGATIVE |
| IBS4 | F | 31 | IBS | Solid | ACTIVE | 0.074 | NEGATIVE |
| IBS5 | F | 72 | IBS | Semi-Solid | ACTIVE | 0.079 | NEGATIVE |
| IBS6 | F | 47 | IBS | Solid | ACTIVE | 0.088 | NEGATIVE |
| IBS7 | F | 19 | IBS | Semi-Solid | ACTIVE | 0.105 | NEGATIVE |
| IBS8 | F | 58 | IBS | Semi-Solid | ACTIVE | 0.107 | NEGATIVE |
| IBS9 | F | 40 | IBS | Solid | ACTIVE | 0.065 | NEGATIVE |
| IBS10 | F | 33 | IBS | Semi-Solid | ACTIVE | 0.065 | NEGATIVE |
| IBS11 | F | 78 | IBS | Solid | ACTIVE | 0.071 | NEGATIVE |
| IBS12 | F | 74 | IBS | Semi-Solid | ACTIVE | 0.063 | NEGATIVE |
| IBS13 | F | 50 | IBS | Semi-Solid | ACTIVE | 0.052 | NEGATIVE |
| IBS14 | F | 39 | IBS | Solid | ACTIVE | 0.079 | NEGATIVE |
| IBS15 | F | 54 | IBS | Solid | ACTIVE | 0.080 | NEGATIVE |
| IBS16 | M | 49 | IBS | Semi-Solid | ACTIVE | 0.238 | POSITIVE |
| IBS17 | M | 53 | IBS | Solid | ACTIVE | 0.123 | NEGATIVE |
| IBS18 | F | 34 | IBS | Solid | ACTIVE | 0.091 | NEGATIVE |

TABLE 5-continued

Clinical data and test results for irritable bowel syndrome patients

| Patient ID | Sex | Age | Disease | Stool consistency | Disease Activity | Optical Density | Fecal ASCA |
|---|---|---|---|---|---|---|---|
| IBS19 | F | 43 | IBS | Solid | ACTIVE | 0.075 | NEGATIVE |
| IBS20 | F | 35 | IBS | Solid | ACTIVE | 0.075 | NEGATIVE |
| IBS21 | F | 51 | IBS | Semi-Solid | ACTIVE | 0.081 | NEGATIVE |
| IBS22 | F | 40 | IBS | Solid | ACTIVE | 0.083 | NEGATIVE |

There were a total of 49 patients with Crohn's disease and 37 with ulcerative colitis. In the Crohn's disease group, a total of 55.1% patients were positive for fecal ASCA. In the ulcerative colitis group, 13.5% were positive. Of the 22 IBS patients, a single patient (4.6%) was positive for fecal ASCA. All 12 healthy controls were negative. A summary of positive results for fecal ASCA is shown in Table 6.

TABLE 6

Summary of positive results for Crohn's disease, ulcerative colitis, active IBS, and healthy controls

| Total Assessments N = 120 | Total | Fecal ASCA Positive | Fecal ASCA Negative |
|---|---|---|---|
| Total IBD (Crohn's disease and ulcerative colitis) | 86 | 37.2% (32) | 62.8% (54) |
| Total Crohn's Disease | 49 | 55.1% (27) | 44.9% (22) |
| Total Ulcerative Colitis | 37 | 13.5% (5) | 86.5% (32) |
| Total Active IBS | 22 | 4.6% (1) | 96.4% (21) |
| Total Healthy Controls | 12 | 0 | 100.0% (12) |

When distinguishing Crohn's disease from ulcerative colitis, fecal ASCA exhibited a sensitivity of 55.1% and specificity of 86.5%. The predictive positive and negative values were 84.4% and 59.3%, respectively, and the correlation was 68.6% as shown in Table 7.

TABLE 7

Statistical evaluation using the presence of fecal ASCA to distinguish Crohn's disease from ulcerative colitis

| N = 86 | Crohn's disease | Ulcerative colitis |
|---|---|---|
| Fecal ASCA positive | 27 | 5 |
| Fecal ASCA negative | 22 | 32 |
| Sensitivity | 55.1% | |
| Specificity | 86.5% | |
| Predictive Positive Value | 84.4% | |
| Predictive Negative Value | 59.3% | |
| Correlation | 68.6% | |

When distinguishing Crohn's disease from ulcerative colitis, irritable bowel syndrome and healthy controls, fecal ASCA exhibited a sensitivity of 55% and a specificity of 91.6%. The predictive positive and negative values were 82% and 75%, respectively, and the correlation was 77% as shown below in Table 8.

TABLE 8

Statistical evaluation using fecal ASCA to distinguish Crohn's disease from ulcerative colitis, irritable bowel syndrome/healthy controls

| N = 120 | Crohn's disease | UC/IBS/Healthy Controls |
|---|---|---|
| Fecal ASCA positive | 27 | 6 |
| Fecal ASCA negative | 22 | 65 |
| Sensitivity | 55.1% | |
| Specificity | 91.6% | |
| Predictive Positive Value | 81.8% | |
| Predictive Negative Value | 74.7% | |
| Correlation | 76.7% | |

The mean optical densities for each group were obtained and differences were tested for statistical significance using a two-tailed t-test giving a p-value result. Of the 33 patients that tested positive for fecal ASCA, there were 27 CD, 5 UC, and 1 IBS. Sensitivity, specificity and overall correlation were 55.1%, 91.5% and 76.7%, respectively. ASCA-positive CD showed a higher mean±SD A450 of 1.183±0.794 as compared to 0.382±0.113 for UC and the single A450 of 0.0.091±0.0.038 for IBS. There was a significant difference between CD and all other subject groups. A summary of the statistical analysis is listed in Table 9.

TABLE 9

Summary of the Mean and P values of Optical Densities for Fecal ASCA

| Test Group | Mean Optical Density | Standard Deviation | Optical Density Range | P Value |
|---|---|---|---|---|
| CD | 1.183 | 0.794 | 0.341–3.000 | CD vs UC, IBS, HC $P < 0.005$ |
| UC | 0.382 | 0.113 | 0.382–0.113 | CD vs UC $P < 0.05$ |
| IBS | 0.091 | 0.038 | 0.052–0.238 | CD vs IBS $P < 0.005$ |
| HC | 0.091 | 0.019 | 0.054–0.124 | CD vs HC $P < 0.005$ |

EXAMPLE 2

In this example, the sensitivity of the fecal ASCA test was determined using serial two fold dilutions of highly purified ASCA antibodies. For the analysis, standard curves were generated using the kit diluent. The test was consistently positive at a concentration of 0.62 μg/mL as determined by a cutoff absorbency value of ≧0.200. Individual results are shown below in Table 10. The standard curves are shown in FIG. 1.

TABLE 10

Standard curves generated using purified ASCA antibodies

| Purified ASCA Antibodies (µg/mL) | Test 1 | Test 2 | Mean | Std Dev |
|---|---|---|---|---|
| 5.00 | 1.702 | 1.856 | 1.779 | 0.108 |
| 2.50 | 1.117 | 1.099 | 1.108 | 0.012 |
| 1.25 | 0.634 | 0.624 | 0.629 | 0.007 |
| 0.62 | 0.303 | 0.329 | 0.316 | 0.018 |
| 0.31 | 0.191 | 0.164 | 0.177 | 0.019 |
| 0.16 | 0.115 | 0.113 | 0.114 | 0.001 |
| 0.08 | 0.090 | 0.077 | 0.083 | 0.009 |
| 0.04 | 0.063 | 0.065 | 0.064 | 0.001 |

EXAMPLE 3

In this example, tests were conducted to determine what type of immunoglobulins (antibodies) were present in a fecal sample and in serum. The immunglobulin typing was done for human IgA, human IgA$_{sec}$, human IgD, human IgM, and human IgG. The immunoglobulin typing was done on a fecal sample from 6 Crohn's disease patients and 2 ulcerative colitis and on a serum control sample using pre-absorbed Ig-type specific conjugates. The serum control sample was obtained from a patient with a confirmed allergy to *Saccharomyces cerevisiae*.

Of the Crohn's disease patients, 5 patients exhibited a response to IgA and IgA$_{sec}$, 4 patients exhibited a response to IgM and a single patient exhibited a response to IgG. Of the 2 ulcerative colitis patients, a single patient reacted with the Ig conjugate. The serum control only exhibited a response to individual immunoglobulins IgM and IgG. A response to IgA and IgA$_{sec}$ occurred the fecal samples but not in the control serum sample. A summary of results are shown in Table 11.

In summary, the present embodiment of the invention provides a method and apparatus for the differentiation of Crohn's disease from other gastrointestinal illnesses, such as ulcerative colitis and irritable bowel syndrome, using the presence of fecal anti-*Saccharomyces cerevisiae* antibodies (ASCA) as a marker for Crohn's disease. The apparatus includes an enzyme-linked immunoassay or other immunoassay that utilizes antibodies specific to human immunoglobins for the measurement of total endogenous ASCA in a human fecal sample. The method and apparatus may be used by healthcare providers to distinguish Crohn's disease from other gastrointestinal illnesses, such as ulcerative colitis and irritable bowel syndrome. The present embodiment of the invention has been described in relation to particular embodiments which are intended in all respects to be illustrative rather than restrictive. Alternative embodiments will become apparent to those skilled in the art to which the present embodiment of the invention pertains without departing from its scope.

From the foregoing, it will be seen that this embodiment of the invention is one well adapted to attain all the ends and objects hereinabove set forth together with other advantages which are obvious and which are inherent to the method.

It will be understood that certain features and subcombinations are of utility and may be employed without reference to other features and subcombinations. This is contemplated by and is within the scope of the claims.

Having thus described the invention, what is claimed is:

1. A method for diagnosing Crohn's disease, the method comprising:
   obtaining a fecal sample from a person; and
   determining whether the fecal sample contains an elevated level of endogenous anti-*Saccharomyces cerevisiae* antibodies, wherein an elevated level of the endogenous anti-*Saccharomyces cerevisiae* antibodies is an indicator of Crohn's disease.

2. The method of claim 1, wherein the elevated level of the endogenous fecal anti-*Saccharomyces cerevisiae* antibodies differentiates Crohn's disease from ulcerative colitis.

3. The method of claim 1, wherein elevated level of the fecal endogenous anti-*Saccharomyces cerevisiae* antibodies differentiates Crohn's disease from irritable bowel syndrome.

TABLE 11

A Summary of Immunoglobulin Typing of ASCA in a Human Fecal sample and a Serum Control

| Patient Number | Disease | IgA Conjugate | IgA$_{sec}$ Conjugate | IgD Conjugate | IgM Conjugate | IgG Conjugate | Ig Conjugate |
|---|---|---|---|---|---|---|---|
| 1 | Crohn's Disease | + | + | − | + | + | + |
| 2 | Crohn's Disease | + | + | − | + | − | + |
| 3 | Crohn's Disease | − | − | − | − | − | − |
| 4 | Crohn's Disease | + | + | NO DATA | + | − | + |
| 5 | Crohn's Disease | + | + | NO DATA | − | − | + |
| 6 | Crohn's Disease | + | + | NO DATA | + | − | + |
| 7 | Ulcerative Colitis | − | − | − | − | − | − |
| 8 | Ulcerative Colitis | − | − | − | − | − | + |
| Serum Control | Yeast Allergy | − | − | − | + | + | + |

4. The method of claim 1, wherein the endogenous fecal anti-*Saccharomyces cerevisiae* antibodies comprise the total anti-*Saccharomyces cerevisiae* antibodies.

5. The method of claim 1, wherein the endogenous fecal anti-*Saccharomyces cerevisiae* antibodies comprise secretory IgA.

6. The method of claim 1 further comprises diluting the fecal sample.

7. The method as recited in claim 6, wherein the diluting step comprises diluting the fecal sample to 1:20 dilution.

8. The method of claim 6, wherein the determination of the elevated level of the endogenous fecal anti-*Saccharomyces cerevisiae* antibodies in the sample includes contacting the fecal sample with an extract of *Saccharomyces cerevisiae* to create a treated sample.

9. The method of claim 8, wherein the step of determining the elevated level of the endogenous fecal anti-*Saccharomyces cerevisiae* antibodies further includes contacting the treated sample with enzyme-linked polyclonal antibodies to create a readable sample.

10. The method of claim 9, wherein the step of determining the elevated level of the endogenous fecal anti-*Saccharomyces cerevisiae* antibodies further includes determining the optical density of the readable sample at 450 nm, wherein the optical density corresponds to an elevated level of the anti-*Saccharomyces cerevisiae* antibodies in the readable sample.

11. The method of claim 10, wherein if the optical density of the readable sample is greater than or equal to 0.200, the fecal sample is determined to have an elevated level of the endegenous anti-*Saccharomyces cerevisiae* antibodies.

12. The method of claim 1, wherein the fecal sample includes human feces and mucosal secretions.

13. A diagnostic assay for diagnosing Crohn's disease comprising:

obtaining a human fecal sample;

diluting the fecal sample;

contacting the fecal sample with an extract *Saccharomyces cerevisiae* to create a treated sample;

contacting the treated sample with enzyme-linked polyclonal antibodies to create a readable sample;

adding an enzyme substrate for color development to the readable sample; and determining the optical density of the readable sample at 450 nm to determine whether the readable sample contains an elevated level of endogenous anti-*Saccharomyces cerevisiae* antibodies as compared to a reference value for healthy patients.

14. The diagnostic assay of claim 13, wherein the elevated level of the endogenous anti-*Saccharomyces cerevisiae* antibodies is an indicator of Crohn's disease.

15. The diagnostic assay of claim 14, wherein an optical density of the readable sample greater than or equal to 0.200 at 450 nm is an indicator of the presence of an elevated level of the endogenous anti-*Saccharomyces cerevisiae* antibodies in the fecal sample.

* * * * *